(12) United States Patent
Tu et al.

(10) Patent No.: US 10,508,234 B2
(45) Date of Patent: Dec. 17, 2019

(54) MANUFACTURING, UTILIZATION, AND ANTIFOULING COATING OF HYDROXYL-COVERED SILICON QUANTUM DOT NANOPARTICLE (71) Applicant: NATIONAL CHIAO TUNG UNIVERSITY, Hsinchu (TW)

(72) Inventors: Chang-Ching Tu, New Taipei (TW); Kuang-Po Chen, Taoyuan (TW); Yaw-Kuen Li, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 190 days.

(21) Appl. No.: 15/440,596

(22) Filed: Feb. 23, 2017

(65) Prior Publication Data
US 2017/0240808 A1  Aug. 24, 2017

Related U.S. Application Data (60) Provisional application No. 62/299,334, filed on Feb. 24, 2016.

(51) Int. Cl.
| G01N 33/552 | (2006.01) |
| G01N 33/543 | (2006.01) |
| C09K 11/59 | (2006.01) |
| C09K 11/02 | (2006.01) |
| C09D 5/16 | (2006.01) |
| C09D 189/00 | (2006.01) |
| G01N 33/58 | (2006.01) |
| C09D 7/65 | (2018.01) |

(52) U.S. Cl.
CPC ............ *C09K 11/59* (2013.01); *C09D 5/1637* (2013.01); *C09D 5/1662* (2013.01); *C09D 7/65* (2018.01); *C09D 189/00* (2013.01); *C09K 11/025* (2013.01); *G01N 33/588* (2013.01)

(58) Field of Classification Search
None
See application file for complete search history.

(56) References Cited

U.S. PATENT DOCUMENTS

2009/0308441 A1* 12/2009 Nayfeh ............ H01L 31/02167
136/256

OTHER PUBLICATIONS

Tu et al. Fluorescent porous silicon biological probes with high quantum efficiency and stability. Optics Express 2014, vol. 22, Issue 24, pp. 2996-30003. (Year: 2014).*

(Continued)

Primary Examiner — Shafiqul Haq
(74) Attorney, Agent, or Firm — Muncy, Geissler, Olds & Lowe, P.C.

(57) ABSTRACT

A hydroxyl-covered silicon quantum dot nanoparticle having a silicon core, a plurality of silicon quantum dots, and a plurality of hydrocarbon chains is illustrated. A first portion of a surface associated with the silicon core is passivated by a plurality of silicon hydroxyl groups (Si—OH). The silicon quantum dots are attached to a second portion of the surface associated with the silicon core. The hydrocarbon chains are bonded to each of the silicon quantum dots through a plurality of silicon carbide bonds (Si—C), wherein each termination of the hydrocarbon chains has a carbon hydroxyl group (C—OH), such that the hydroxyl-covered silicon quantum dot nanoparticle is thoroughly covered by the carbon hydroxyl groups (C—OH) and the silicon hydroxyl groups (Si—OH).

7 Claims, 5 Drawing Sheets (56) References Cited

OTHER PUBLICATIONS

Hau et al. Efficient surface grafting of luminescent silicon quantum dots by photoinitiated hydrosilylation. Langmuir 2005, vol. 21, pp. 6054-6062. (Year: 2005).*

Emoto et al. Stability of poly(ethylene glycol) graft coatings. Langmuir 1998, vol. 14, pp. 2722-2729. (Year: 1998).*

* cited by examiner

MANUFACTURING, UTILIZATION, AND ANTIFOULING COATING OF HYDROXYL-COVERED SILICON QUANTUM DOT NANOPARTICLE

CROSS-REFERENCE TO RELATED APPLICATION

This application claims priority from U.S. Provisional Application No. 62/299,334, filed on Feb. 24, 2016, in USPTO, the content of which is hereby incorporated by reference in their entirety for all purposes.

BACKGROUND OF THE INVENTION

1. Technical Field

The present disclosure relates to a quantum dot nanoparticle used in immunofluorescence applications, and particularly to a hydroxyl-covered silicon quantum dot nanoparticle used in the immunofluorescence applications, a method of manufacturing the hydroxyl-covered silicon quantum dot nanoparticles, and an antifouling coating of the hydroxyl-covered silicon quantum dot nanoparticle.

2. Description of the Related Art

Organic chemical fluorescent dyes can be used in immunofluorescence imaging applications, for example, vitro cell imaging, vivo cell imaging, tumor cell targeting, flow cytometry, and clinical intraoperative fluorescence guided surgery. The organic chemical fluorescent dyes can be fluorescent proteins or fluorescent peptides, which have low toxicity, even no toxicity, but the organic chemical fluorescent dyes cannot have the sufficient chemical stability, such that the photobleaching phenomenon occurs. Therefore, organic chemical fluorescent dyes are not suitable to be used for long-term or time-lapse immunofluorescence imaging applications.

To have the property of anti-photobleaching, the quantum dot particles were proposed to be used in immunofluorescence imaging applications. Currently, the quantum dot particles implemented in immunofluorescence imaging applications are mostly II-VI or III-V compound semiconductors, such as CdSe or InP compound semiconductor that contains heavy metallic elements and poses a certain level of toxicity. Although, coatings that are biocompatible wrapped around on the outer surface of the quantum dot particles can prevent leakage of the heavy metals and ease the acute biological toxicity, however, their long-term effect on the living organisms is still unclear, thus limiting its potential development and diagnostic implementations.

SUMMARY OF THE INVENTION

In view of the aforementioned problems existing in prior art, the objective of the present disclosure is to provide a hydroxyl-covered silicon quantum dot nanoparticle, a method of manufacturing the hydroxyl-covered silicon quantum dot nanoparticles, an antifouling coating of the hydroxyl-covered silicon quantum dot nanoparticle, and a time-gated immunofluorescence imaging applications using the hydroxyl-covered silicon quantum dot nanoparticles.

In order to achieve at least one of the above objects, the present disclosure provides a hydroxyl-covered silicon quantum dot nanoparticle comprising a silicon core, a plurality of silicon quantum dots, and a plurality of hydrocarbon chains. A first portion of a surface associated with the silicon core is passivated by a plurality of silicon hydroxyl groups (Si—OH). A plurality of silicon quantum dots are attached to a second portion of the surface associated with the silicon core. The hydrocarbon chains are bonded to each of the silicon quantum dots through a plurality of silicon carbide bonds (Si—C), wherein each termination of the hydrocarbon chains has a carbon hydroxyl group (C—OH), such that the hydroxyl-covered silicon quantum dot nanoparticle is thoroughly covered by a plurality of carbon hydroxyl groups (C—OH) and a plurality of silicon hydroxyl groups (Si—OH).

In order to achieve at least one of the above objects, the present disclosure provides an antifouling coating substantially encapsulating the aforementioned hydroxyl-covered silicon quantum dot nanoparticle. The antifouling coating is composed of a plurality of proteins and a plurality of polyethylene glycols.

In order to achieve at least one of the above objects, the present disclosure provides a method of manufacturing a plurality of hydroxyls-covered silicon quantum dot nanoparticles, which comprises steps as follows. A surface of a silicon wafer is electrochemically etched to provide a plurality of silicon cores, wherein each of the silicon cores has a plurality of silicon quantum dots attached thereto. The silicon quantum dots are photochemically hydrosilylated to provide a plurality of hydrosilylated silicon quantum dots, wherein each of the hydrosilylated silicon quantum dots has a plurality of hydrocarbon chains bonded thereto and each of the bonded hydrocarbon chains has a carbon hydroxyl group (C—OH) termination. The plurality of silicon cores are released from the surface of the silicon wafer to provide a plurality of released silicon cores. The released silicon cores are high energy ball milled to provide a plurality of crumbled silicon cores, wherein each of the crumbled silicon cores has a first surface portion passivated with a plurality of silicon hydroxyl groups (Si—OH) and a second surface portion attached with the hydrosilylated silicon quantum dots. The crumbled silicon cores are selectively etched to provide a plurality of etched silicon cores, wherein only the first surface portion of each crumbled silicon core is etched and the second surface portion of each crumbled silicon core is protected by the hydrosilylated silicon quantum dots.

In order to achieve at least one of the above objects, the present disclosure provides a time-gated immunofluorescence imaging method using the above hydroxyl-covered silicon quantum dot nanoparticles.

As stated above, the hydroxyl-covered silicon quantum dot nanoparticle illustrated in the present disclosure to be used in immunofluorescence imaging applications, has one or more of the following advantages.

(1) The hydroxyl-covered silicon quantum dot nanoparticle has a high water solubility, high photoluminescence quantum yield (PLQY), size-dependent photoluminescence characteristic, narrower emission linewidth, wider excitation spectrum, and large-scale Stokes shift, and therefore is suitable to be used in immunofluorescence imaging applications, for instance, a time-gated immunofluorescence imaging method.

(2) The hydroxyl-covered silicon quantum dot nanoparticle has a high water solubility, high pho The hydroxyl-covered silicon quantum dot nanoparticle has no toxicity and, therefore, can be used for in vitro cell imaging and can further be used for in vivo cell imaging, tumor cell targeting, and clinical intraoperative fluorescence guided surgery.

(3) The hydroxyl-covered silicon quantum dot nanoparticle has a high water solubility, high pho The hydroxyl-covered silicon quantum dot nanoparticle can be a biodegradable label and not only can be used for in vitro cell imaging and can further be used for in vivo cell imaging, tumor cell targeting, and clinical intraoperative fluorescence guided surgery.

(4) The hydroxyl-covered silicon quantum dot nanoparticle has a high water solubility, high pho The hydroxyl-covered silicon quantum dot nanoparticle has the characteristics of anti-photobleaching and, therefore, can be more suitably used for long-term or time-lapse immunofluorescence imaging applications.

(5) The hydroxyl-covered silicon quantum dot nanoparticle has a high water solubility, high pho The hydroxyl-covered silicon quantum dot nanoparticle can be encapsulated by the antifouling coating, and antibodies can be attached on the surface of antifouling coating, such that the hydroxyl-covered silicon quantum dot nanoparticle can target the specific cell, and can be used in the long-term or time-lapse immunofluorescence imaging applications.

DETAILED DESCRIPTION OF THE EXEMPLARY EMBODIMENTS

For the committee members to better understand the novel features, contents, and advantages of the present disclosure and the effect thereof that can be achieved, detailed descriptions of the present disclosure are provided as follows, accompanied by diagrams and preferred embodiments. The diagrams and exemplary embodiments used are mainly for the purpose of illustration and explanation of the patent specification, without necessarily implying the actual size, ratio, and precise configuration. Therefore, the accompanied diagrams, size, ratio and configuration shall not be interpreted in a way to limit the scope of rights in actual implementation of the present disclosure, and thus must be explained first.

Please note that although certain vocabularies such as "first", "second" and "third" are used in the text to represent various elements, these described elements shall not be limited by and rely on the naming method and wording. These terms are used to distinguish different elements. Therefore, a "first" element described below can be expressed as a "second" element without departing from the scope of the present disclosure.

The embodiment of the present disclosure illustrates a hydroxyl-covered silicon quantum dot nanoparticle having a silicon core, a plurality of silicon quantum dots forming on portion of the surface of the silicon core. Other one portion of the surface associated with the silicon core is passivated by a plurality of silicon hydroxyl groups (Si—OH); and the plurality of silicon quantum dots are bonded to a plurality of hydrocarbon chains through a plurality of silicon carbide bonds (Si—C). Therefore, the surface chemistry of the hydroxyl-covered silicon quantum dot nanoparticle is formed by hydroxyl groups (including carbon hydroxyl groups and silicon hydroxyl groups).

In order to targeting a specimen for conducting immunofluorescence imaging applications, the embodiment of the present disclosure also provides an antifouling coating, composed of a plurality of protein and a plurality of polyethylene glycols, for substantially encapsulating the hydroxyl-covered silicon quantum dot nanoparticle. The surface chemistry structure of the antifouling coating can be also connected to antibodies for capturing the antigens corresponding to the antibodies. In addition, the embodiments of the present disclosure also provide a manufacturing method of the hydroxyl-covered silicon quantum dot nanoparticle and a time-gated immunofluorescence imaging method using the hydroxyl-covered silicon quantum dot nanoparticles.

Figure 1:
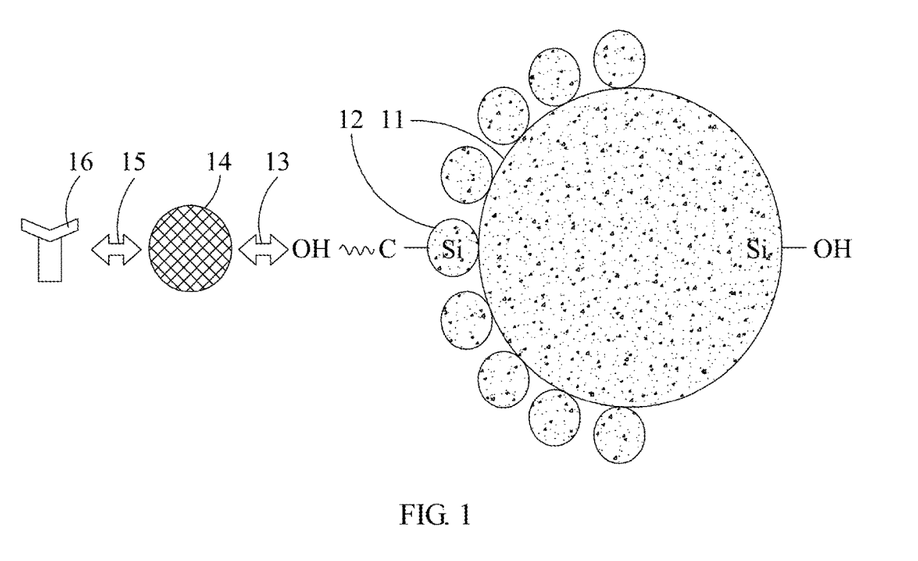
FIG. 1 illustrates a schematic diagram of the composition of a hydroxyl-covered silicon quantum dot nanoparticle of the embodiment of the present disclosure.

Please refer to FIG. 1. FIG. 1 illustrates a schematic diagram of the composition of a hydroxyl-covered silicon quantum dot nanoparticle of the embodiment of the present disclosure. The hydroxyl-covered silicon quantum dot nanoparticle shown in FIG. 1 comprises a silicon core 11, a plurality of silicon quantum dots 12, and a plurality of hydrocarbon chains. The first portion of a surface associated with the silicon core 11 does not have silicon quantum dots attached thereto, and a plurality of silicon quantum dots 12 are attached to the second portion of the surface associated with the silicon core 11, wherein the second portion is opposite to the first portion. In this embodiment, the diameter of the silicon core 11 is about 10 nanometers to 10 micrometers, for instance 130 nanometers, and the diameter of the silicon quantum dot 12 is less than 10 nanometers.

The first portion of the surface associated with the silicon core 11 is passivated by a plurality of silicon hydroxyl groups (Si—OH). It is noted that, in order to simplify the diagram, only one silicon (Si) particle connected to a hydrocarbon chain in the first portion of the surface associated with the silicon core 11 is illustrated in FIG. 1. However, the present disclosure is not limited thereto.

For the plurality of silicon quantum dots 12 attached to the second portion of the surface associated with the silicon core 11, a plurality of hydrocarbon chains are bonded to each of the silicon quantum dots 12 through a plurality of silicon carbide bonds (Si—C), wherein each termination of the hydrocarbon chains has a carbon hydroxyl group (C—OH), such that the hydroxyl-covered silicon quantum dot nanoparticle is thoroughly covered by a plurality of carbon hydroxyl groups (C—OH) and a plurality of silicon hydroxyl groups (Si—OH). Please note that, in order to simplify the diagram, only one silicon quantum dot 12 having the carbon hydroxyl group attached to the surface thereof is illustrated. However, the present disclosure is not limited thereto. Furthermore, the aforementioned hydrocarbon chains include 10-Undecen-1-ol. However, the present disclosure is not limited thereto.

The hydroxyl-covered silicon quantum dot nanoparticle can be used in immunofluorescence imaging applications. When a specific specimen needs to be targeted and the fouling problem needs to be resolved, it is preferably to use the antifouling coating made of proteins 14 and polyethylene glycols 15 to substantially encapsulate the hydroxyl-covered silicon quantum dot nanoparticle, wherein the antifouling coating is hydrophilic. The aforementioned immunofluorescence imaging applications include, at least one application of, vitro cell imaging, vivo cell imaging, tumor cell targeting, flow cytometry, and clinical intraoperative fluorescence guided surgery, and the present disclosure do not limit the applications of hydroxyl-covered silicon quantum dot nanoparticles.

In the embodiment of the present disclosure, the protein 14 of antifouling coating can contain bovine serum albumin and the present disclosure is not limited thereto. The protein 14 of antifouling coating is connected to the hydroxyl-covered silicon quantum dot nanoparticle through a plurality of chemical linkers 13. The chemical linkers 13 include p-Toluenesulfonyl chloride, 2,2'-(Ethylenedioxy)-diethanethiol, and 1-(2-Isothiocyanatoethyl)-1H-pyrrole-2,5-dione, and the present disclosure is not limited thereto. In addition, p-Toluenesulfonyl chloride in the chemical linker 13 can be used to prepassive the hydroxyl group on the surface associated with the silicon quantum dot 12.

Each of polyethylene glycols 15 has isothiocyanate (—N=C=S) terminations at its two ends. The first end of the polyethylene glycol 15 is connected to the protein 14 through isothiocyanate-amine coupling, and the second end of the polyethylene glycol 15 is connected to the antibody 16 through isothiocyanate-amine coupling, such that the antigen corresponding to the antibody 16 is targeted in the immunofluorescence imaging applications. For example, the antibody 16 can target the anti-HER2 antigen corresponding to the Human Epidermal Growth Factor Receptor 2 (HER2). However, the present disclosure does not limit the type of antibody 16. Please note that, in order to simplify the diagram, only one silicon quantum dot 12 connected a protein 14 and only one protein 14 connected to an antibody 16 are illustrated in FIG. 1. However, the present disclosure is not limited thereto.

In the embodiment of the present disclosure, when the concentration of the hydroxyl-covered silicon quantum dot nanoparticles is 1600 mcg/ml during the vitro cell activity test, the biocompatibility thereof is higher and the toxicity thereof to cells is very low. In addition, excited by the ultraviolet radiation with a wavelength about 365 nanometers (that is to inject an excitation pulse light onto the specimen), the colloid solution of hydroxyl-covered silicon quantum dot nanoparticles will emit red fluorescence, wherein the photoluminescence quantum yield thereof can reach 45-55% in the organic solution, and 5-10% in buffer solution.

Using confocal fluorescence microscopy imaging and flow cytometry analysis, if the anti-HER2 antibody is chosen as antibody 16, the hydroxyl-covered silicon quantum dot nanoparticles can express noticeable specific binding among ovarian cancer cell SKOV3 with HER2 in larger scale and can express negligible nonspecific binding among Chinese hamster ovary cell (CHO) without HER2. Under the similar experimental conditions, the outcome of immunofluorescence experiments show that the performance of hydroxyl-covered silicon quantum dot nanoparticles is equivalent to that of fluorescein isothiocyanate (FITC).

Figure 2:
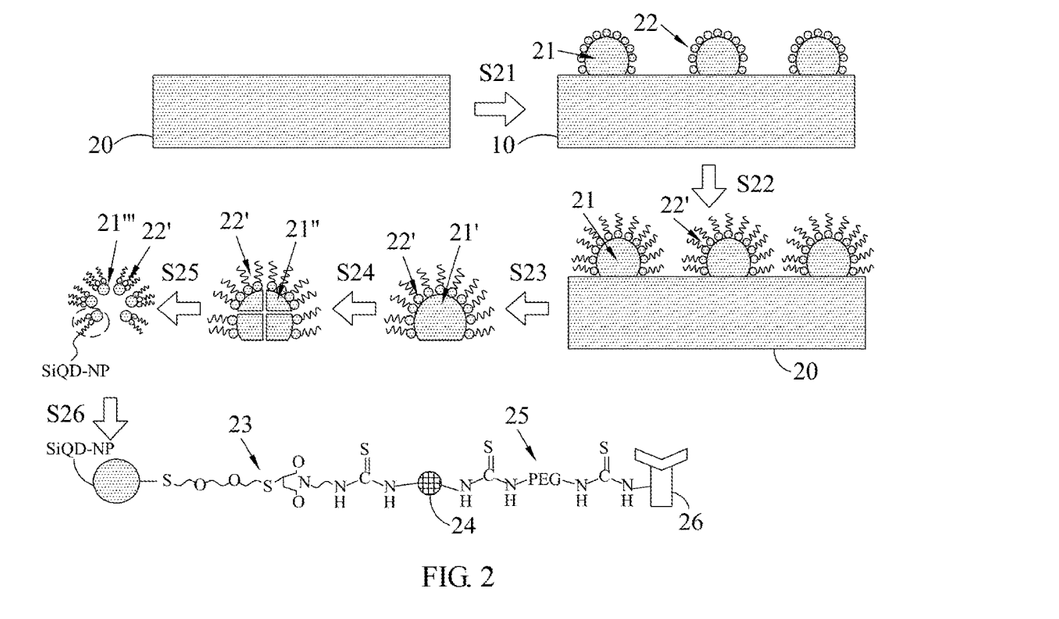
FIG. 2 illustrates a schematic diagram of the method of manufacturing the hydroxyl-covered silicon quantum dot nanoparticles of the embodiment of the present disclosure.

Please refer to FIG. 2. FIG. 2 illustrates a schematic diagram of the method of manufacturing the hydroxyl-covered silicon quantum dot nanoparticles of the embodiment of the present disclosure. First, in step S21, the surface of the silicon wafer 20 is electrochemically etched to provide a plurality of silicon cores 21, wherein the plurality of silicon cores 21 have a plurality of silicon quantum dots 22 attached thereto. The silicon wafer 20 can be a P-type silicon wafer of 6 inches in diameter. However, the present disclosure is not limited thereto. Furthermore, one of implementation methods of step S21 is to electrochemically etch the surface of the silicon wafer 20 at a constant current in electrolyte of methanol and hydrogen fluoride (HF). However, the present disclosure is not limited thereto.

Next, in step S22, a plurality of silicon quantum dots 22 are photochemically hydrosilylated to provide a plurality of hydrosilylated silicon quantum dots 22', wherein each of the plurality of hydrosilylated silicon quantum dots 22' has a plurality of hydrocarbon chains bonded thereto and each termination of the plurality of bonded hydrocarbon chains has a carbon hydroxyl group (C—OH), and the plurality of hydrocarbon chains include 10-Undecen-1-ol. One of implementation methods of step S22 is to photochemically hydrosilylate a plurality of silicon quantum dots 22 in an oxygen free environment under white light illumination. However, the present disclosure is not limited thereto.

Next, in step S23, a plurality of silicon cores 21 are released from the surface of the silicon wafer 20 to provide a plurality of released silicon cores 21'. One of implementation methods of step S23 is to perform the porous silicon layer smash and collection on the silicon wafer 20 to remove the block portion of the silicon wafer 20. However, the present disclosure is not limited thereto.

Next, in step S24, the plurality of released silicon cores 21' are processed by high energy ball milling to provide a plurality of crumbled silicon cores 21", wherein the surface associated with each of the plurality of crumbled silicon cores 21" has a first portion passivated by a plurality of silicon hydroxyl groups (Si—OH) and a second portion attached by a plurality of hydrosilylated silicon quantum dots 22'. Please note that, in step S24, the hydrosilylated silicon quantum dots 21' can be dissolved in isopropyl alcohol first, and then the high energy ball milling is performed afterward. However, the present disclosure is not limited thereto.

Next, in step S25, a plurality of crumbled silicon cores 21" are selectively etched to provide a plurality of etched silicon cores 21''', wherein only the first portion of the surface of each crumbled silicon core 21" is etched and the second portion of the surface of each crumbled silicon core 21" is protected by a plurality of hydrosilylated silicon quantum dots 22'. One of implementation methods of step S25 is to selectively etch the crumbled silicon cores 21" in aqueous solution of nitric acid ($HNO_3$) and hydrogen fluoride (HF). However, the present disclosure is not limited thereto. Therefore, step S25 can produce hydroxyl-covered silicon quantum dot nanoparticles SiQD-NP without being encapsulated by antifouling coating.

Next, in step S26, the antifouling coating is formed. The antifouling coating is used for substantially encapsulating the hydroxyl-covered silicon quantum dot nanoparticle SiQD-NP and made of proteins 24 and polyethylene glycols 25. The proteins 24 include bovine serum albumin and are connected to hydroxyl groups through chemical linkers to thoroughly cover the hydroxyl-covered silicon quantum dot nanoparticle SiQD-NP. Each of polyethylene glycols 25 has a plurality of isothiocyanate (—N=C=S) terminations at both ends thereof. The first end of the polyethylene glycol 25 is connected to the protein 24 through isothiocyanate-amine coupling and the second end of the polyethylene glycol 25 is connected to the antibody 26 through isothiocyanate-amine coupling.

Figure 3:
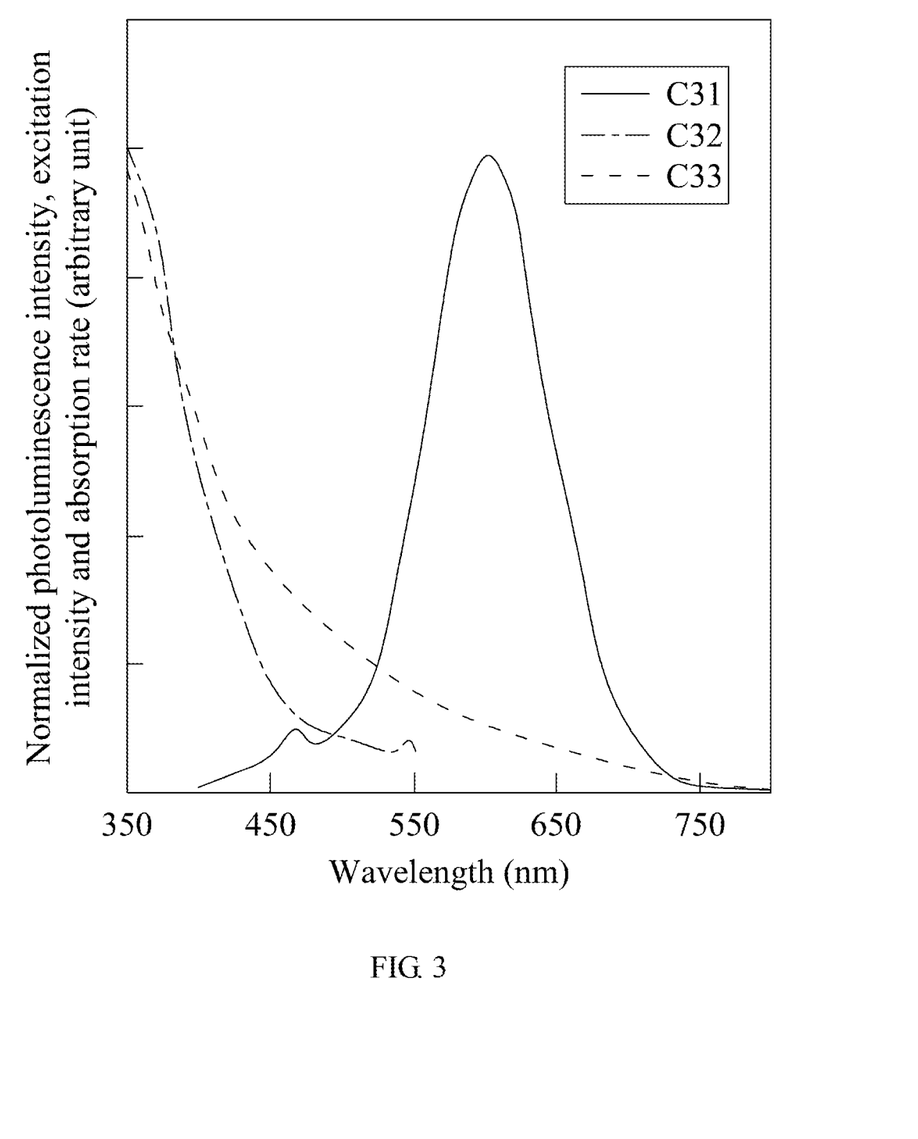
FIG. 3 illustrates the curves of the normalized photoluminescence intensity, excitation intensity and absorption rate of the hydroxyl-covered silicon quantum dot nanoparticle in the embodiment of the present disclosure.

Please refer to FIG. 3. FIG. 3 illustrates the curves of the normalized photoluminescence intensity, excitation intensity and absorption rate of the hydroxyl-covered silicon quantum dot nanoparticle in the embodiment of the present disclosure. In the embodiment of the present disclosure, the curves of the normalized photoluminescence intensity, excitation intensity and absorption rate of the hydroxyl-covered silicon quantum dot nanoparticle are curves C31~C33 respectively. Curves C31~C33 show that the hydroxyl-covered silicon quantum dot nanoparticles can absorb excitation pulse light in wavelength of 350 nanometers, and have a photoluminescence peak at about 600 nm to 700 nm after the excitation pulse light is injected.

Figure 4:
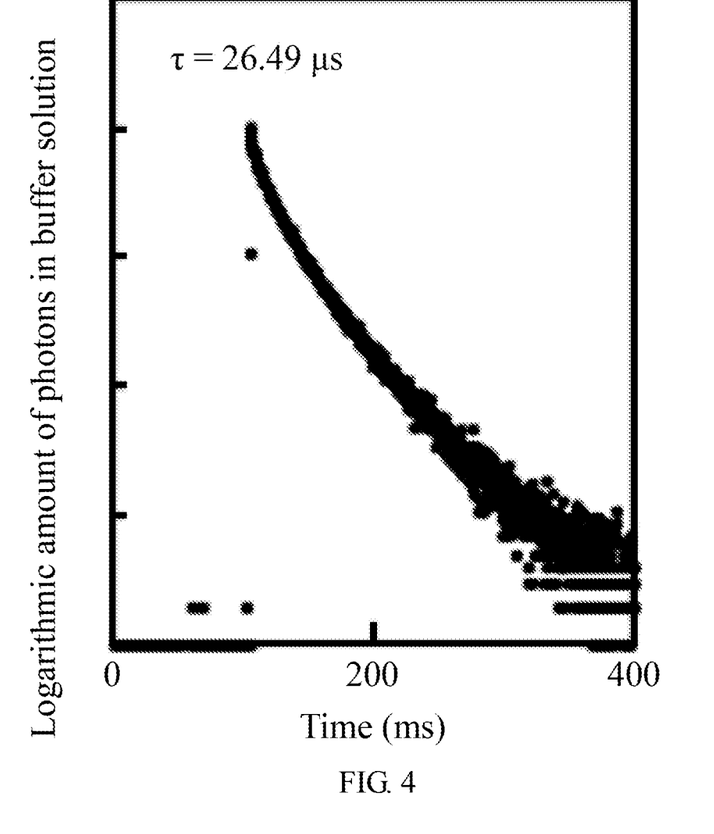
FIG. 4 illustrates the curve of the logarithmic amount and the photoluminescence lifetime of the photons in the buffer solution, wherein the photons are generated by exciting the hydroxyl-covered silicon quantum dot nanoparticle in the embodiment of the present disclosure.

Please refer to FIG. 4. FIG. 4 illustrates the curve of the logarithmic amount and the photoluminescence lifetime of the photons in the buffer solution, wherein the photons are generated by exciting the hydroxyl-covered silicon quantum dot nanoparticle in the embodiment of the present disclosure After the hydroxyl-covered silicon quantum dot nanoparticles are excited, the hydroxyl-covered silicon quantum dot nanoparticles generate multiple photons distributing in the range of about 600 to 700 nanometers of wavelength. Most of photons in buffer solution have a photoluminescence lifetime of 26.49 microseconds (ms). Therefore, it is estimated that photons have a photoluminescence lifetime cycle of about 25 microseconds.

Figure 5:
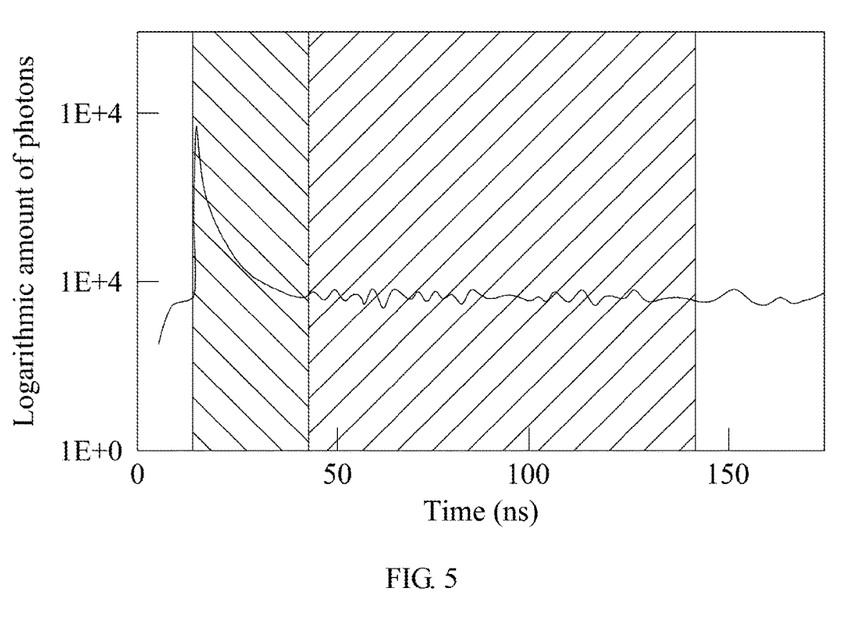
FIG. 5 illustrates the curve of the logarithmic amount and the time of the photons on a main imaging region after the photons are generated by exciting the combination of SKOV3 ovarian cancer cells and the hydroxyl-covered silicon quantum dot nanoparticle in the embodiment of the present disclosure.

Please refer to FIG. 5. FIG. 5 illustrates the curve of the logarithmic amount and the time of the photons on a main imaging region after the photons are generated by exciting the combination of SKOV3 ovarian cancer cells and the hydroxyl-covered silicon quantum dot nanoparticle in the embodiment of the present disclosure. According to FIG. 5, there are 104 photons at 20 nanometers, and after 50 nanoseconds, the logarithmic amount of photons in the main imaging zone still can reach 2 (i.e. 102 photons) that can continue beyond 150 nanoseconds.

Accordingly, the hydroxyl-covered silicon quantum dot nanoparticle in the embodiment of the present disclosure can be used in time-gated immunofluorescence imaging method. The aforementioned time-gated immunofluorescence imaging method is to inject the excitation pulse light through the designed optical system onto the specimen, apply an imaging time slot is delayed about 50 nanoseconds to 50 microseconds to form the image (note: image formation is an accumulation of photons within the imaging time slot), so that only the fluorescence photons emitted from the hydroxyl-covered silicon quantum dot nanoparticles are captured.

In summary, the hydroxyl-covered silicon quantum dot nanoparticle of the embodiment of the present disclosure has the low toxicity, high water solubility, anti-foulness, specificity to specimens, and characteristics of anti-photobleaching, and therefore, can be used in immunofluorescence imaging applications.

The examples described above are a few preferred embodiments of the present disclosure. Alternative embodiments will become apparent to those skilled in the art to which the present disclosure described in the patent specification and the appended claims pertains without departing from its spirit and scope.

What is claimed is:

1. A method of manufacturing a plurality of hydroxyl-covered silicon quantum dot nanoparticles, comprising:
 (a) electrochemically etching a surface of a silicon wafer to provide a plurality of silicon cores, wherein each of the silicon cores has a plurality of silicon quantum dots attached thereto;
 (b) photochemically hydrosilylating the silicon quantum dots to provide a plurality of hydrosilylated silicon quantum dots, wherein each of the hydrosilylated silicon quantum dots has a plurality of hydrocarbon chains bonded thereto and each of the bonded hydrocarbon chains has a carbon hydroxyl group (C—OH) termination;
 (c) releasing the plurality of silicon cores from the surface of the silicon wafer after photochemically hydrosilylating the silicon quantum dots to provide a plurality of released silicon cores;
 (d) high energy ball milling the released silicon cores to provide a plurality of crumbled silicon cores, wherein each of the crumbled silicon cores has a first surface portion passivated with a plurality of silicon hydroxyl groups (Si—OH) and a second surface portion attached with the hydrosilylated silicon quantum dots; and
 (e) selectively etching the crumbled silicon cores to provide a plurality of etched silicon cores, wherein only the first surface portion of each crumbled silicon core is etched and the second surface portion of each crumbled silicon core is protected by the hydrosilylated silicon quantum dots.

2. The method as claimed in claim 1, wherein the surface of the silicon wafer is electrochemically etched at a constant current in an electrolyte of methanol and HF.

3. The method as claimed in claim 1, wherein the silicon wafer is P-type.

4. The method as claimed in claim 1, wherein the silicon quantum dots are photochemically hydrosilylated in an oxygen free environment under white light illumination.

5. The method as claimed in claim 1, wherein the hydrocarbon chains include 10-Undecen-1-ol.

6. The method as claimed in claim 1, wherein the crumbled silicon cores are selectively etched in a solution of $HNO_3$ and HF.

7. The manufacturing method as claimed in claim 1, wherein the manufacturing method further includes:
 (f) forming antifouling coatings substantially encapsulating the hydroxyl-covered silicon quantum dot nanoparticles after selectively etching the crumbled silicon cores, wherein the antifouling coatings are composed of a plurality of proteins and a plurality of polyethylene glycols.

* * * * *